United States Patent [19]

Tranjan et al.

[11] Patent Number: 4,974,601

[45] Date of Patent: Dec. 4, 1990

[54] PORTABLE HEART MONITOR PERFORMING MULTIPLE FUNCTIONS

[75] Inventors: Farid M. Tranjan, Charlotte, N.C.; Mohammed Said, Washington, D.C.; Bharati Vadhar, Edison, N.J.; Paul Sandok, Charlotte, N.C.

[73] Assignee: University of North Carolina at Charlotte, Charlotte, N.C.

[21] Appl. No.: 244,964

[22] Filed: Sep. 5, 1988

[51] Int. Cl.$^5$ .............................................. A61B 5/04
[52] U.S. Cl. ................................... 128/696; 128/706; 128/700; 128/680
[58] Field of Search ............... 128/695, 696, 700, 702, 128/706, 708, 680

[56] References Cited

U.S. PATENT DOCUMENTS

| | | | |
|---|---|---|---|
| 3,837,333 | 9/1974 | Bruckheim | 128/2.06 F |
| 3,841,315 | 10/1974 | Kopp | 128/706 |
| 3,861,387 | 1/1975 | Lawhorn et al. | 128/2.06 A |
| 4,066,069 | 1/1978 | Dolch | 128/2.06 F |
| 4,129,125 | 12/1978 | Lester | 128/2.05 R |
| 4,193,393 | 3/1980 | Schlager | 128/710 |
| 4,404,974 | 9/1983 | Titus | 128/670 |
| 4,499,904 | 2/1985 | Sidorenko | 128/703 |
| 4,622,979 | 11/1986 | Katchis | 128/702 |
| 4,630,204 | 12/1986 | Mortara | 128/696 |
| 4,679,144 | 7/1987 | Cox et al. | 364/417 |
| 4,680,708 | 7/1987 | Ambos et al. | 364/217 |
| 4,796,620 | 1/1989 | Imran | 128/702 |
| 4,805,629 | 2/1989 | Farges | 128/700 |

Primary Examiner—Francis Jaworski
Assistant Examiner—George Manuel
Attorney, Agent, or Firm—Bell, Seltzer, Park & Gibson

[57] ABSTRACT

A method and apparatus for monitoring multiple aspects of a patient's cardiac condition which is portable microprocessor based, and can be programmed to select (for storage in random access memory (RAM)) anomalous heartbeat waveforms while rejecting normal waveforms. In addition, the cardiac monitor gives real time warnings of erratic heartbeat waveforms and stores these waveforms for future analysis. The cardiac monitor also detects and energizes an alarm signal if a patient's heartbeat skips a predetermined number of beats.

13 Claims, 3 Drawing Sheets

PORTABLE HEART MONITOR PERFORMING MULTIPLE FUNCTIONS

FIELD OF THE INVENTION

This invention generally relates to the monitoring of various multiple aspects of a primate patient's cardiac condition in a portable device providing storage of vital cardiac information and an indication of anomalous cardiac conditions.

BACKGROUND OF THE INVENTION

Previous cardiac monitors performed only a few monitoring activities and were therefore unsuitable for many monitoring functions. For example, some monitors such as Ambos et al. U.S. Pat. No. 4,680,708, store heartbeat waveforms and generate an average waveform therefrom but do not compare these average waveforms or detect anomalies as the instant invention does.

In monitors that make a comparison between an incoming waveform and a stored waveform, none disclose use of the average waveform for the stored waveform For example, the information stored in Lester et al. U.S. Pat. No. 4,129,125 is merely of "normal" readings programmed into the ROM by operator.

Some monitors, like Schlager U.S. Pat. No. 4,193,393, while having the capability to store anomalous heartbeat waveforms, as this invention does, do not have the ability to compare incoming and average pulse rates and energize an alarm when a predetermined number of beats are skipped As can be seen, the prior art does not have the capability to perform a multiple of important monitoring activities required for thorough surveillance of primate cardiac patients. Consequently, there is a great need for a cardiac monitoring device which can supply all needed monitoring functions in an inexpensive, compact and easy to use device.

OBJECT AND SUMMARY OF THE INVENTION

The instant invention provides for a portable cardiac monitoring device and method performing a combination of functions valuable in the care and surveillance of primate cardiac patients This unique device can be programmed to select, for storage in RAM, anomalous waveforms, while rejecting normal waveforms. In addition, real time warning of erratic heartbeat waveforms is available with storage of the same, with reference to time of occurrence and pulse rate, for future analysis.

This data is immediately available for analysis The invention also generates an average or current pulse rate signal and compares that signal to an incoming pulse rate signal to determine when a predetermined number of heartbeats are skipped and then energizes an alarm signal.

Accordingly, it is an object of the present invention to provide a portable cardiac monitoring device that is able to perform a combination of valuable cardiac surveillance functions with only a single device.

Another object of the present invention is to provide a cardiac monitoring device which can provide real time warning of erratic heartbeats and anomalous waveforms.

It is a further object of the invention to store anomalous waveforms with reference to time of occurrence and pulse rate for future analysis.

It is a further object of the present invention to generate and store an average pulse rate signal and compare that signal with an incoming pulse rate signal to give real time warning of a patient skipping a predetermined number of beats.

Other objects, advantages and novel features of the present invention will become apparent from the following detailed description of the invention when viewed with reference to the drawings.

PREFERRED EMBODIMENT OF THE INVENTION

Figure 1:
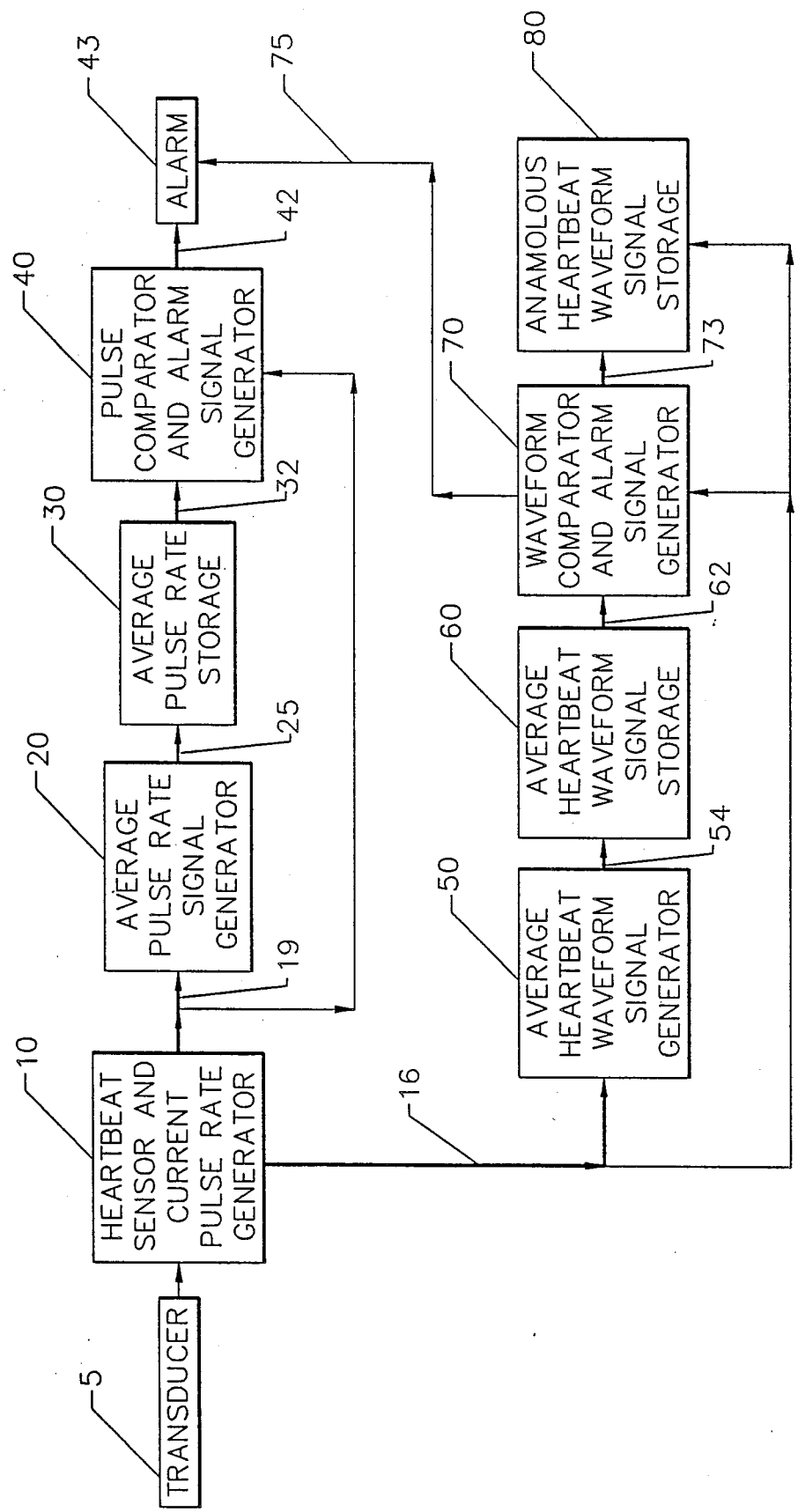
FIG. 1 is a block diagram of the components providing the cardiac monitoring functions.

FIG. 1 illustrates in block form the components performing the multiple functions of the cardiac monitor. The heartbeat is sensed by a conventional transducer 5 and the electric signal generated thereby is received by the heartbeat sensor and current pulse rate generator 10. A current pulse signal is generated on line 19 and received by the average pulse rate signal generator 20. An average pulse rate signal is generated on line 25 and received by the average pulse rate storage device 30. A pulse comparator and alarm signal generator 40 receives the current pulse signal on line 19 and the average pulse rate signal on line 32 as stored in storage device 30.

The heartbeat sensor and current pulse rate generator also generates a current heartbeat waveform signal on line 16 that is received by the average heartbeat waveform signal generator 50. An average heartbeat waveform signal is generated on line 54 and received by the average heartbeat waveform signal storage device 60. A waveform comparator and alarm signal generator 70 receives the current heartbeat waveform signal on line 16 and the average heartbeat waveform signal on line 62 as stored in storage device 60. An anomalous heartbeat waveform signal storage device 80 also receives the current heartbeat waveform signal on line 16 and an enabling signal on line 73 from the waveform comparator 70. An alarm 43 receives an alarm enabling signal on line 42 from the pulse comparator 40 or on line 75 from the waveform comparator 70.

Figure 2:
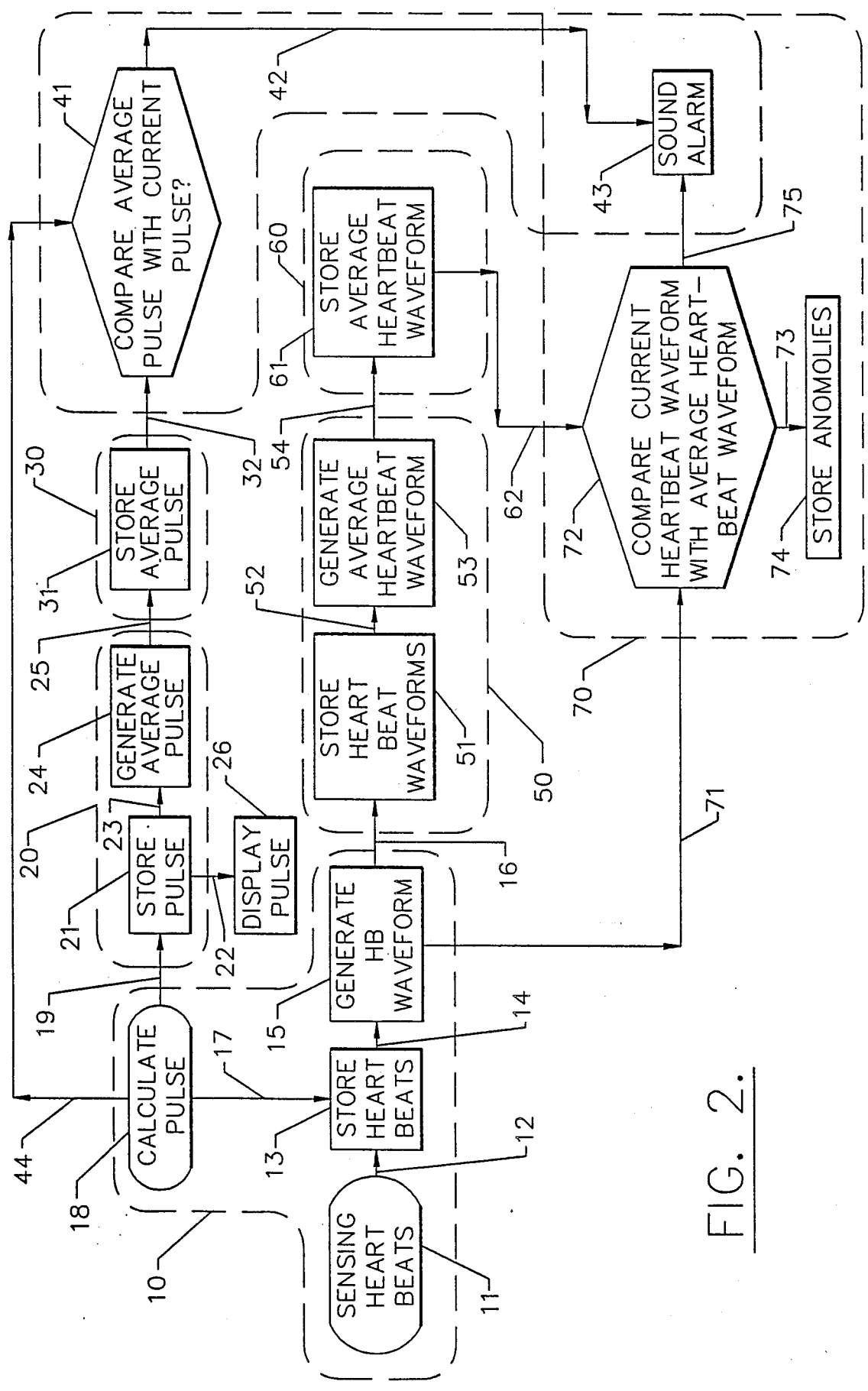
FIG. 2 is a detailed block diagram and flow chart of the method of providing the cardiac monitoring functions.

FIG. 2 is a detailed block diagram and flow chart describing the present invention's method for performing its various functions. The heartbeat sensor 11, such as a transducer, senses the individual heartbeats and generates an electric signal for each on line 12. The heartbeat storage 13 stores the heartbeat signals over time, for access on lines 14 and 17. Unit 15 generates an average heartbeat waveform by chronologically assembling the number of heartbeats per unit time, and placing the signal on line 16 and 71. Further information regarding the heartbeat signals is included later. Unit 18 calculates a patient's current pulse rate from the signals it receives over line 17. The signal representing the pulse rate is placed on lines 19 and 44.

Unit 21 stores the current pulse rate signals it receives over time and makes the signal available on lines 22 and 23. Unit 24 generates an average pulse rate signal over time from the signals it receives over line 23. The time span for determining the average pulse rate may vary, or be set, as necessary or desirable. Alternatively, the average pulse may be re-determined to reflect a change in the pulse rate as the patient's body becomes more, or less, active. Unit 24 places its output along line 25. Display 26 is an optional device which displays a representation of the current pulse rate signal from the signal it receives along line 22. It may be, for example, a liquid crystal or light emitting diode array.

Unit 31 stores the average pulse signal it receives over line 25 and makes the stored signal available over line 32.

Unit 41 compares the stored average pulse rate signal on line 32 with the incoming current pulse rate signal on line 44 to determine if a predetermined number of heartbeats X, are skipped in the incoming signal on line 12. If the incoming pulse signal 44 indicates that the patient's heart has skipped a specified number of beats X, unit 41 sends a signal out over line 42 that energizes the alarm 43.

Returning to the heartbeat signal on line 16, unit 51 stores the heartbeat waveforms it receives and makes its output signal available on line 52. Unit 53 generates an average heartbeat waveform from the signals it receives. The time span or number of waveforms for determining an average waveform may vary, or be set, as necessary or desirable. Alternatively, the average waveform may be re-determined to reflect a change in heart activity. Unit 53 transmits an average heartbeat waveform signal over line 54.

Unit 61 stores the average heartbeat waveform signal it receives along line 54 and transmits the average heartbeat waveform signal along line 62.

Unit 72 compares the current heartbeat waveform received along line 71 with the average heartbeat waveform received along line 62 to see if the waveforms differ by more than a predetermined amount Y. If so unit 72 sends out signals along lines 73 and 75. The signal on line 73 enables unit 74, causing it to store the anomalous waveform signal that differed by an amount Y, and the signal on line 75 triggers the alarm 43.

Figure 3:
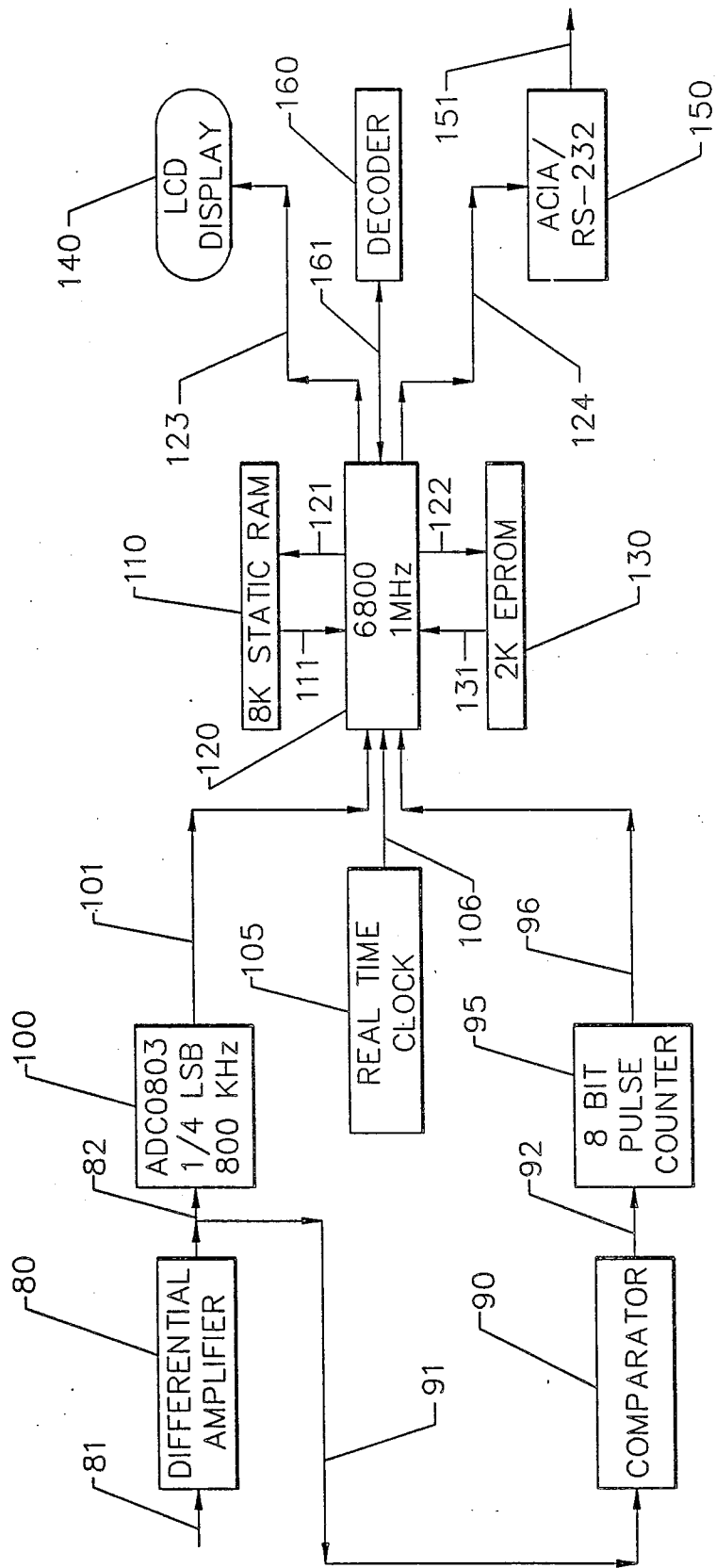
FIG. 3 is a block diagram of the components of the cardiac monitoring device.

Referring now to FIG. 3, the signal representing the patient's heartbeat is sensed and enters the system through line 81. The differential amplifier 80 receives the signal along line 81, amplifies it and outputs an amplified heartbeat signal along line 82. Line 91 splits off line 82 and carries the amplified heartbeat signal into the comparator 90 which converts the signal to a square wave and transmits the square wave representing the heartbeats of the patient along line 92. The pulse counter 95 calculates the patient's pulse rate and transmits a signal representing the pulse on line 96 for processing in the microprocessor 120.

The analog-to-digital converter 100 receives the amplified heartbeat signal from line 82 and converts it to a digital signal and transmits the converted signal along line 101 for processing in the microprocessor 120.

The real time clock 105 provides signals along line 106 to the microprocessor. In the preferred embodiment the real time clock provides a signal each minute.

The static RAM 110, preferably having 8K of memory space available, stores the anomalous heartbeat waveforms, the average heartbeat waveform, and the average pulse rate of the patient. The RAM 110 receives this information along line 121 and transmits the stored information to the microprocessor 120 along line 111. The EPROM 130 stores the program for operation of the microprocessor and any constants, such as X and Y. The EPROM 130 preferably has 2K of memory and the EPROM receives information from the microprocessor 120 along line 122 and transmits information along line 131.

The microprocessor 120 is preferable a Motorola 6800 operating at 1 megahertz. The microprocessor sends current pulse rate signals along line 123 to the liquid crystal display 140 which displays a representation of the patient's current pulse rate. The microprocessor 120 sends information to the interface adaptor 150 along line 124.

The chip enable decoder 160 receives signals from the microprocessor along line 161. The decoder 160 decodes addresses from the microprocessor to enable the RAM 110, EPROM 130 and LCD display 140. The decoder is preferably a dual 2 to 4 bit decoder. The interface adaptor 150 provides communication with any system outside the heart monitor system such as a personal computer, for example. The interface adapter 150 permits the dumping of RAM contents into a PC for immediate analysis along line 151.

The preferred components include:

| | |
|---|---|
| differential amplifier | 353 U18A1 |
| comparator | 353 01852 |
| analog to digital converter | 0803 |
| pulse counter | 74LS393 |
| real time clock | ATC 58321 |
| microprocessor | Motorola 6800 |
| static RAM | 6204P12 |
| EPROM | U10 |
| decoder | 74139 |
| computer time clock | 6875A |
| interface | RS-232 |
| LED display | MSM1416 |

Referring to FIG. 2, in operation, the portable heart monitor senses 11 and stores the patient's heartbeat. From the stored heartbeats a pulse is calculated 18, stored 21, and displayed 26. From the stored pulse 21 an average pulse is generated 24 and stored 31. The stored average pulse 31 and the incoming pulse 18 are compared 41 and if a predetermined number of heartbeats are skipped an alarm is energized 43.

The stored heartbeats 13 are also used to generate heartbeat waveforms 15 which are stored 51. From the stored heartbeats 51 an average heartbeat waveform is generated 53 and stored 61. The stored average heartbeat waveform 61 is compared 72 to the current heartbeat waveform and any waveforms differing by more than a predetermined value Y will be stored 74 and an alarm will be energized 43.

In the drawings and specification, there has been set forth a preferred embodiment of the invention, and although specific terms are employed, they are used in a generic and descriptive sense only and not for purposes of limitation.

That which is claimed is:

1. An apparatus for monitoring multiple aspects of a patient's cardiac condition comprising:
    (a) means for generating a present pulse signal indicative of a patient's present pulse rate and a present heartbeat waveform signal;
    (b) means for receiving the present pulse signal and generating an average pulse rate signal indicative of the pulse rate over a predetermined period of time;
    (c) means for storing the average pulse rate signal;

(d) means for comparing the present pulse signal and the average pulse rate signal and generating an alarm signal if the difference between these signals exceeds a first predetermined threshold;

(e) means for receiving the present heartbeat waveform signal and generating an average heartbeat waveform signal indicative of the patient's average heartbeat over a predetermined period of time;

(f) means for storing the average heartbeat waveform signal;

(g) means for comparing the present heartbeat waveform signal and the average heartbeat waveform signal and generating an alarm signal if the difference between these signals exceeds a second predetermined threshold; and (h) means for storing the present heartbeat waveform signal indicative of the patient's present heartbeat that resulted in the generation of an alarm signal.

2. The apparatus of claim 1 wherein the means for generating a present signal indicative of a patient s present pulse rate and a present heartbeat waveform signal comprises:

means for sensing a patient's heartbeat and generating a signal representing the patient's heartbeat;

means for storing the signal representing the patient's heartbeat;

means for storing the signal representing the patient's heartbeat;

means for generating the heartbeat waveform signal from the stored heartbeat signal and;

means for calculating a pulse rate from the stored heartbeat signal.

3. The apparatus of claim 1 wherein the means for receiving the present pulse signal and generating an average pulse rate signal comprises:

means for storing the present pulse signal and generating an average pulse rate signal therefrom.

4. The apparatus of claim 1 wherein the apparatus further comprises:

means for displaying a representation of the present pulse signal indicating the present pulse rate.

5. The apparatus of claim 1 wherein the means for generating an average heartbeat waveform comprises:

means for storing a plurality of present heartbeat waveform signals and generating an average electric heartbeat waveform signal therefrom.

6. The apparatus of claim 1 wherein the means for generating a present pulse signal indicative of a patient's present pulse rate and present heartbeat waveform comprises:

a transducer for generating an analog signal representative of a patient's present heartbeat;

means for amplifying the analog signal; and means for converting the amplified analog signal to a digital signal.

7. The apparatus of claim 1 wherein the means for receiving the present pulse signal and generating an average pulse rate signal indicative of the patient's pulse rate comprises:

means for converting heartbeat signals into a square waveform signal; and means for calculating a pulse rate from a square waveform signal.

8. A method for monitoring multiple aspects of a patient's cardiac condition comprising:

(a) generating a present pulse signal indicative of a patient's current pulse rate and a present heartbeat waveform signal;

(b) generating an average pulse rate signal indicative of the patient's pulse rate over a predetermined period of time;

(c) storing the average present pulse rate signal;

(d) comparing the present pulse signal and the average pulse rate signal and generating an alarm signal if the difference between these signals exceeds a first predetermined threshold;

(e) receiving the present heartbeat waveform signal and generating an average heartbeat waveform signal indicative of the patient's average heartbeat over a predetermined period of time;

(f) storing the average heartbeat waveform signal;

(g) comparing the present heartbeat waveform signal and the average heartbeat waveform signal and generating an alarm signal if the difference between these signals exceeds a second predetermined threshold; and (h) storing the present heartbeat waveform signal indicative of the patient's current heartbeat that resulted in the generation of an alarm signal.

9. The method of claim 8 further comprising:
displaying a numerical representation of the present pulse signal indicating the present pulse rate.

10. The method of claim 8 wherein the step of generating an average pulse rate signal comprises:
storing the present heartbeat waveform signals and generating the average pulse rate signal therefrom.

11. The method of claim 8 wherein the step of generating an average heartbeat waveform comprises:
storing the present heartbeat waveform signals and generating an average electric heartbeat waveform signal therefrom over a predetermined period of time.

12. The method of claim 8 wherein the step of generating a present pulse signal indicative of a patient's current pulse rate and a present heartbeat waveform comprises:

sensing the patient's heartbeat and generating a heartbeat signal;

storing the heartbeat signals;

generating a heartbeat waveform from the stored heartbeat signals; and calculating a pulse rate from the stored heartbeat signals.

13. The method of claim 8 wherein the step of receiving the present pulse signal and generating an average pulse rate signal comprises:
storing the present pulse signal and generating an average pulse rate signal therefrom.

* * * * *